US005665332A

United States Patent [19]
Mundschenk et al.

[11] Patent Number: 5,665,332
[45] Date of Patent: Sep. 9, 1997

[54] SYSTEM FOR DELIVERING FOAMS CONTAINING MEDICAMENTS

[75] Inventors: David D. Mundschenk, Dania, Fla.; Albert Saferstein, Armonk; Gary Gerard Fores, Sea Cliff, both of N.Y.

[73] Assignee: OralCare Systems, Inc., Virginia Beach, Va.

[21] Appl. No.: 218,796

[22] Filed: Mar. 28, 1994

[51] Int. Cl.$^6$ ............................................. A61K 7/16
[52] U.S. Cl. .................. 424/49; 424/44; 424/53; 424/56; 424/58; 424/616
[58] Field of Search ................. 514/578; 424/56, 424/616, 44, 49, 53, 58; 252/104, 552; 222/1, 190

[56] References Cited

U.S. PATENT DOCUMENTS

| | | | |
|---|---|---|---|
| D. 315,496 | 3/1991 | Pettengill | D9/373 |
| 3,422,993 | 1/1969 | Boehm et al. | 424/53 |
| 4,010,872 | 3/1977 | Lozano et al. | 222/94 |
| 4,657,758 | 4/1987 | Goldemberg | 424/49 |
| 4,666,708 | 5/1987 | Goldemberg | 424/49 |
| 4,687,663 | 8/1987 | Schaeffer | 424/52 |
| 4,836,422 | 6/1989 | Rosenberg | 424/49 |
| 4,964,539 | 10/1990 | Mueller | 222/94 |
| 5,020,694 | 6/1991 | Pettengill | 222/137 |
| 5,038,963 | 8/1991 | Pettengill et al. | 222/145 |
| 5,048,750 | 9/1991 | Tobler | 222/189 |
| 5,059,417 | 10/1991 | Williams et al. | 424/53 |
| 5,084,268 | 1/1992 | Thaler | 424/53 |
| 5,104,644 | 4/1992 | Douglas | 424/53 |
| 5,174,990 | 12/1992 | Douglas | 424/53 |
| 5,176,899 | 1/1993 | Montgomery | 424/50 |
| 5,208,010 | 5/1993 | Thaler | 424/53 |
| 5,294,434 | 3/1994 | King et al. | 424/58 |
| 5,339,988 | 8/1994 | Palmer et al. | 222/190 |
| 5,369,131 | 11/1994 | Poli et al. | 54/772.4 |
| 5,378,465 | 1/1995 | Zeines | 424/195.1 |

OTHER PUBLICATIONS

H. Mintzer, "Aerosols", Chapter 10 in *Pharmaceutical Dosage Forms —Disperse Systems*, Marcel Dekker, Inc. pp. 204–220 (1989).

D. Garlen, "Toothpastes", Chapter 14, pp. 511–532 in *Pharmaceutical Dosage Forms —Disperse Systems*, Marcel Dekker, Inc. 1989.

"Surfactants in Oral Hygiene Products", pp. 299–347 in *Surfactants in Cosmetics*, M. Reiger ed., Marcel Dekker, Inc. 1985.

*CRC Handbook of Food, Drug and Cosmetic Excipients*, S. Smolinske, pp. 359–362 (1992).

P. Barkvoll. ("Should toothpastes foam? Sodium lauryl sulfate —a toothpaste detergent in focus", Norske Tannlaegeforenings Tidende 99(3)82–4 (1989)) (Abstract only).

"Mouthwashes and Gargles", p. 1680, in American Hospital Formulary Services —Drug Information 1992, G. McEvoy et al. eds., American Society of Hospital Pharmacists.

*Primary Examiner*—Brian M. Burn
*Attorney, Agent, or Firm*—Collard & Roe, P.C.

[57] ABSTRACT

A system for delivering a chemical agent in the form of a foam, which in its preferred embodiment involves the use of a propellantless dispenser to deliver a formulation containing both an anionic surface active agent such as sodium lauryl sulfate as a foaming agent and hydrogen peroxide as a disinfecting chemical agent.

18 Claims, No Drawings

SYSTEM FOR DELIVERING FOAMS CONTAINING MEDICAMENTS

TECHNICAL FIELD

The present invention relates to devices useful for the delivery of medicaments and other formulations in the form of lathers and foams. In another aspect, the invention relates to formulations useful in the oral cavity, such as dentifrices containing hydrogen peroxide. In yet another aspect, the invention relates to the pharmacological use of surfactants such as anionic surfactants, and in particular sodium lauryl sulfate.

BACKGROUND ART

Delivery Devices

Formulations such as cosmetics and pharmaceuticals can be dispensed in a wide variety of vehicles and forms, including powders, capsules, liquids, aerosols, and the like. In particular, the delivery of formulations by the aerosol route is generally considered to take one of three forms: (1) the use of "space sprays", such as spray insecticides and air fresheners, which produce very free sprays capable of evaporating rapidly or floating in the air; (2) the use of sprays such as hair sprays and deodorants, that are intended for continuous film formation; and (3) the use of aerated foams, such as shaving creams, which are produced by the rapid expansion of a propellant through an emulsion.

A variety of dispensers have been described for the purpose of delivering formulations of these various types. See, e.g., H. Mintzer, "Aerosols", Chapter 10 in *Pharmaceutical Dosage Forms - Disperse Systems*, Marcel Dekker, Inc. pp. 204–220 (1989. Aerosols for oral and nasal therapy are generally said to incorporate medicaments as solids suspended in a propellant. More recent advances in valve and propellant technology are said to provide improved delivery to the throat and nasal areas. Formulations delivered in aerosol form by the use of such devices can often include the use of surfactants. For instance, surfactants are commonly used in nebulizer vehicles to decrease surface tension and thus affect particle size (Mintzer, above, p. 206).

Yet other types of aerosol containers, pressurized with nitrogen, have been used to dispense toothpaste through a dip tube and foam-style valve. For a variety of reasons, however, such containers have not been commercially successful. See, e.g., D. Garlen, "Toothpastes", Chapter 14, pp. 511–532 in *Pharmaceutical Dosage Forms - Disperse Systems*, Marcel Dekker, Inc. 1989. As a result, various forms of "pump" dispensers have been developed for delivering toothpaste, the pumps relying on the use of a spring device to force the toothpaste out of a spout.

Tobler, in U.S. Pat. No. 5,048,750 describes an apparatus that is capable of producing and dispensing foams. The apparatus involves the use of a mounting section covered by a cap that can be displaced from an open position to a closed position. The mixing section involves the use of a pervious planer and air and liquid passages directed to the mixing element.

Surfactants

On a separate subject, a large number of surfactants, including sodium lauryl sulfate ("SIS"), have been widely used and found safe in a variety of cosmetic products, including dentrifices. See, e.g., "Surfactants in Oral Hygiene Products", pp. 299–347 in *Surfactants in Cosmetics*, M. Reiger ed., Marcel Dekker, Inc. 1985.

As of 1992, SIS itself was present in over 500 oral solid dosage forms approved by the FDA, as well as in 11 oral liquid dosage forms, 38 topical creams, lotions, ointments, medicates sponges or shampoos, and 28 dentrifices. *CRC Handbook of Food, Drug and Cosmetic Excipients*, S. Smolinske, pp. 359–362 (1992). The usefulness of sodium lauryl sulfate as a synthetic detergent in toothpaste has been studied in a recent article by P. Barkvoll. ("Should toothpastes foam? Sodium lauryl sulfate - a toothpaste detergent in focus", Norske Tannlaegeforenings Tidende 99(3)82–4 (1989)).

U.S. Pat. Nos. 4,657,758 and 4,666,708, for instance, describe dental rinses for loosening plaque and preventing plaque build-up. The rinses described in both patents rely on the detersive effect of oral surfactants. The '708 patent describes the use of SLS as one such oral surfactant, and further describes its function as a "potentiator" for other ingredients. In the Examples, patients were instructed to use one tablespoon of various rinses. Such rinse products, which are commercially available under the brand name "Plax", are typically swirled in the mouth in order to produce a weak foaming action.

Hydrogen Peroxide

On yet another subject, hydrogen peroxide is a common ingredient in mouthwashes and gargles. (See, e.g., "Mouthwashes and Gargles", p. 1680, in American Hospital Formulary Services - Drug Information 1992, G. McEvoy et al. eds., American Society of Hospital Pharmacists). Hydrogen peroxide functions as a weak antibacterial agent, a wound cleanser and a deodorant. It also serves a mechanical effect of effervescence and resultant removal of tissue and other debris.

When used as an oral topical, however, hydrogen peroxide is typically administered in the form of a concentrate, solution, or gel. The product is used for cleansing minor wounds, or minor gum inflammation resulting from dental procedures, orthodontic applications, denture irritations, accidental injury and other mouth and gum irritations (e.g., canker sores).

Such beneficial uses of hydrogen peroxide include its use as an oral germicide, cleansing agent and hemostat. It is considered a useful disinfectant for mucous membranes because of its low toxicity. See, e.g., Zinner. D. D., et. al.; Controlled Study of the Clinical Effectiveness of A New Oxygen Gel on Plaque. Oral Debris and Gingival inflammation, *Pharmacol. Ther. Dent.*, October 1970, 1:7–15.

Dental products such as "MentaDent", which was recently introduced by Chesebrough-Ponds, relies on the use of hydrogen peroxide. The commercial product identifies related U.S. Pat. Nos. 4,687,663, 4,964,539, 5,020,694, 5,038,963, 5,059,417, and Design Pat. No. D 315,496. Such patents relate variously to the use of a hydrogen peroxide component with a second component containing sodium bicarbonate; to a dentifrice composition containing, inter alia, hydrogen peroxide and a polyoxyethylene-polyoxypropylene copolymer; to multi-cavity or multi-chamber dispensing containers; and to a design for a dispensing container.

SLS and hydrogen peroxide have, on occasion, been used together in formulations for the oral cavity. See, for instance, U.S. Pat. No. 5,104,644 and 5,174,990 (mouthrinse), 5,084, 268 and 5,208,010 (tooth whitening dentifrice).

There appear however to be few, if any, instances of the use of devices for the propellantless delivery of formulations to the oral cavity in the form of foams, particularly for formulations that incorporate hydrogen peroxide and are used in the oral cavity.

SUMMARY OF THE INVENTION

The present invention provides a system useful for delivering chemical agent-containing formulations in the form of foams. In particular, the invention provides a system for delivering a chemical agent-containing formulation in the form of a foam, the system comprising a propellantless dispenser containing a foamable formulation comprising the chemical agent in the form of a solution or stable suspension and an aqueous solution of an anionic surface active agent as a foaming agent.

In a preferred embodiment, the invention provides a system for delivering a foam such as a disinfecting foam, the system comprising a propellantless dispenser containing a formulation comprising sodium lauryl sulfate as a foaming agent. In a preferred embodiment, the system is used to deliver a cleansing, antiseptic, or disinfecting foam comprising hydrogen peroxide as the active agent. Such a system is particularly well suited for the delivery of hydrogen peroxide to the oral cavity, i.e., as a dental or oral formulation.

It has been found that the delivery of hydrogen peroxide to the oral cavity in the form of a foam improves the effervescence of the formulation and, in turn, improves the removal of tissue and other debris. The formulation is particularly well suited to suspend and foam away food particles and other debris, and then itself be rinsed away quickly. It does not appear that hydrogen peroxide has previously been used for such purposes in the form of a foam, as delivered by means of a propellantless container as described herein.

The system of the present invention is capable of producing dramatic and rapid detergent action in order to instantly provide voluminous quantities of microbubbles from relatively small initial volumes of formulation. This detergent action, in turn, greatly facilitates the effectiveness of the formulation as an oral rinse. The system of the present invention, for instance, can rapidly provide a volume of bubbles from about 2 grams of formulation that is as great or greater than the volume obtained by swirling up to an ounce (e.g., about 25–30 grams) of a product like Plax in the mouth for 30 seconds, as recommended by the manufacturer.

Formulations of the present invention having hydrogen peroxide have also been found to be particularly effective antifungal agents. To the best of Applicants' knowledge, hydrogen peroxide has not heretofore been approved or applied as an antifungal agent, and particularly not in the form of a foamed or foamable composition.

In another aspect, the present invention provides a method of delivering a formulation in the form of a organoleptically acceptable foam, the method comprising the steps of: (1) providing a formulation, comprising a chemical agent to be delivered and sodium lauryl sulfate as a foaming agent, within a propellantless dispenser, and (2) delivering the formulation in the form of a foam by activation of the dispenser.

DETAILED DESCRIPTION

The present invention provides a system for delivering a wide variety of chemical agents in the form of an efficacious foam. As used herein, the following words and terms shall have the meanings ascribed to them:

"system" will refer to a propellantless dispenser containing a foamable formulation;

"foamable formulation" will refer to a solution, e.g., as a single phase liquid or stable dispersion, which is capable of being delivered from a propellantless dispenser in the form of a foam;

"chemical agent" in turn, will refer to the active agent or other agent to be delivered in the form of a foam;

"foam", and inflections thereof, when used as a verb shall refer to the ability of a formulation to form a foam when dispensed a propellantless dispenser, and when used as a noun shall mean a mass of gas bubbles in a liquid-film matrix;

"foaming agent" shall refer to one or more ingredients in a formulation that functions to causing or facilitate the foaming of the formulation when dispensed from a propellantless dispenser; and "dental formulation" shall refer to any foamable formulation useful in or on the mouth or gums (such as dentifrice, mouthwash, gargle, dental liquid), or other nasopharyngeal application.

Preferred foams of the present invention are substantially stable, yet can be readily broken upon agitation. In other words, the foam is substantially stable after it is formed, so long as it is not agitated. An example of such a foam is one that can be dispensed into the palm of the hand and there remain for at least on the order of minutes. Once agitated however, for instance by rubbing the palms together, the foam is readily broken and in fact essentially disappears within a second or two. Preferred foams are similar in appearance and consistency to the suds obtained by the agitation of dishwashing liquids, that is, they are comprised of small bubbles.

While not intending to be bound by theory, it is believed that the unique combination of SLS as a foaming agent within a propellantless dispenser of the type described herein, together with chemical agents such as hydrogen peroxide, provide an optimal combination of such unexpected qualities as deliverability, foaming, effervescence, and cleaning ability.

Dispensers suitable for use in the system of the present invention are typically those that are capable of creating dispensing a formulation in the form of a foam in a propellantless manner. The word "propellantless" will refer herein to the delivery of a foam in a manner that avoids the use of a pressurized gas to achieve rapid expansion of a propellant through an emulsion. Preferred propellantless dispensers are those that rely on the use of compressed air, for instance obtained by squeezing a bottle, as opposed to piston-type or spring-loaded dispensers.

The foam system of the present invention preferably comprises a propellantless dispenser of the type described in U.S. Pat. No. 5,048,750, the disclosure of which is incorporated herein by reference. A preferred dispenser comprises a device for producing and dispensing a foam and a container for the formulation, the device and container being operably connected in such a manner that the dispenser is capable of delivering the foam upon compression of the bottle. As seen in representative FIG. 1 of the '750 patent, and by reference to the appropriate specification, the dispenser involves the use of a bottle having a series of chamber and prechamber areas. The device further involves the use of a membrane capable of closing liquid passages, together with foam outlets, and mixing elements. If the interior chamber of the bottle is placed under pressure by compression of the bottle, a membrane closes the defined liquid passages, liquid rises in a tube, and in turn air is forced through the passages. The liquid flow and air flow impinge on each other in a prechamber, are displaced by a deflection body and are mixed. The mixture passes as a coarse foam through the passages, into a mixing chamber, and through the mixing element before leaving as a foam through a channel via an outlet. Examples of dispensers of the latter type are those available under the tradename "Physiomer jet fort".

A foam system of the present invention comprises a foaming agent, preferably selected from the class of surface active agents known as anionic detergents. Examples of suitable anionic foaming agents include sodium cocomonoglyceride sulfonate, sodium lauryl sarcosinate, sodium dodecyl benzenesulfonate, and miscellaneous other surfactants such as dioctyl sodium sulfosuccinate, sodium lauryl sulfoacetate, sulfolaurate, and the 2-hydroxyalkyl sulfates. See, e.g., "Surfactants in Oral Hygiene Products", pp. 299–347 in *Surfactants in Cosmetics*, M. Reiger ed., Marcel Dekker, Inc. 1985, the disclosure of which is incorporated herein by reference.

A particularly preferred foaming agent is SLS. SLS is itself classified as an emulsifying, wetting, and/or solubilizing agent. SLS is actually a mixture of sodium alkyl sulfates, primarily sodium lauryl sulfate containing not more than a total of 8% of sodium sulfate and sodium chloride. SLS is a long-chain fatty alcohol sulfate, and commercially available forms of SLS involve a mixture of long-chain saturated alkyl alcohols. Oral grades of SLS are generally made from naturally occurring fats and oils, mostly from coconut fatty acids, or the like. Some products are virtually all dodecyl derivative, while others contain mixtures of dodecyl, tetradecyl, and higher derivatives, depending on the degree of fractionation of the original fatty acids.

Such surface active agents, including SLS, are preferably present in the formulation at a final concentration of between about 0.05% and about 5%, and more preferably between about 0.1% and about 1%, by weight, based on the weight of the chemical agent formulation. Formulations containing less than about 0.5% SLS tend to have poor foaming characteristics, while those containing greater than about 5% SLS tend to impart unpleasant taste or other undesirable characteristics to the formulation.

The formulation delivered using a foam system of the present invention preferably comprises a chemical agent. Suitable chemical agents include any compound, solution or molecule that is desired to be delivered as a foam to the body, including any cavity of the body. Examples of chemical agents that can be delivered to the body in the form of a foam include topical analgesics, anesthetics, antibacterials, antibiotics, antifungal agents, antiinflammatory agents (such as salicylates and steroids), antineoplastics, antiparasitics, antipruritics, antiviral agents, biologicals, contraceptives, dental preparations, deodorants, enzymes and digestants, germicides, hemorrhoidal preparations, hormones, minerals, vaginal preparations, and the like.

In a preferred embodiment, the foam system of the present invention is used for the preparation of foams for the application of abradants, antiacne preparations, antibacterials and/or antifungals, antidermatitis preparations, as well as antiherpes, anti-inflammatory, antiperspiration, antipuritics, antipsoriasis, antiseborrhea, or astringent agents, coal tar, depigmenting agents, detergents, emollients, fungicides, keratolytics, moisturizers, pediculicides, photosensitizers, scabicides, skin bleaches, skin protectants, cleansers, steroids, sulfur and salicylic acid, sun screens, vesicants, wart therapeutic agents, wound dressings, and the like.

Particularly preferred is a formulation that contains both hydrogen peroxide (as an anti-infective agent) and glycerin (as a skin or tissue protectant). The combination of hydrogen peroxide and glycerin has been used as effective local therapy for the treatment of pharyngitis, laryngitis, thrush, gingival infection and necrotizing ulcerative gingivitis. The combination, being non-toxic, has been found to be effective as a wide spectrum antibacterial and, as described herein, as an antifungal agent.

When used for treating oral bacterial infections, the combination provides relief from symptoms and serves as an adjunct to systemic therapy. It also relieves pain associated with these conditions, thereby enabling the patient to maintain or resume normal oral intake. The combination cleanses the tissue of debris, soothes irritated tissues and aids in restoring good oral hygiene. Patient acceptance has been good. See, for instance, Williams, J. C.; Topical Therapy in Infections of the Mouth and Pharynx, *Med Times*, 91:332–334 (1963).

Glycerin is quite effective in protecting the skin and buccal membranes of the mouth and oral cavity. FDA monographs, for instance, define glycerin as an "Active Skin Protectant" for use on skin, lips, and the oral cavity.

Similarly, hydrogen peroxide, for instance at a concentration of between about 1% and about 3% by weight, based on the weight of the formulation, is useful as a weak antibacterial agent, a wound cleanser (including suppurating ulcers and local infections), and a deodorant. When used in a dentifrice, hydrogen peroxide is useful for the removal of debris Coy virtue of its effervescence) and in the treatment of pharyngitis and Vincent's stomatitis.

Foam systems of the present invention can be prepared in any suitable manner, using techniques and equipment within the skill of those in the art. See, e.g., D. Garlen, "Toothpastes", Chapter 14, pp. 511–532 in *Pharmaceutical Dosage Forms - Disperse Systems*, Marcel Dekker, Inc. 1989, the disclosure of which is incorporated herein by reference.

A preferred foam system as identified above can be prepared as follows:

(1) the desired ingredients are selected, based upon their known properties;

(2) the ingredients are mixed, together with adjuvants, according to methods within the skill of those in the art;

(3) the compatibilities of ingredients are evaluated for use in preparation and storage;

(4) the stability and potency of ingredients is assured; and (5) the resultant system is properly packaged and labeled for storage, transport, and use.

Foamable formulations can be provided in either of two forms, either as a homogeneous prefabricated formulation that is already contained within a propellantless dispenser, or as a formulation that can optionally be modified (e.g., diluted) for use and added to a propellantless dispenser.

Chemical agents and formulations useful with the system of the present invention can be prepared using a combination of commonly available ingredients identified as "generally recognized as safe" ("GRAS"). The dispenser can be filled and packaged using techniques within the skill of those in the art. For instance, a typical filling ratio is 60% product to 40% compressed air, according to FEA regulations. Special filling heads are used to fill and pressurize the system.

Examples of suitable chemical agents (and their intended use) include the following (percentages are provided on a weight basis, based on the weight of the final formulation):

essential oils, such as perfume oils, particularly in formulations in which the sodium lauryl sulfate serves the additional purpose of holding such oils in solution or stable suspension;

aloe vera (e.g., between about 0.1 and 10 g/100 ml formulation, and preferably between about 0.3 and 1 g/100 ml), used either with or without hydrogen peroxide;

sodium chloride (e.g., at physiological concentrations, generally about 0.9%), for use in treating cold sores and fever blisters and lesions associated with Herpes virus;

hydrogen peroxide (e.g., about 19 to about 15%, preferably about 8% to about 12%).

Suitable solvents for use in preparing a chemical agent solution of the present invention are those that provide an optimal combination of such properties as: the ability to solubilize the desired chemical agent; compatibility with the foam system; and suitability for topical use. An example of a particularly preferred solvent is purified water.

In a particularly preferred embodiment, other adjuvants such as fluoride, buffering agents, stabilizers and preservatives, foaming agents, antioxidants, flavorings, colors, viscosity modifiers, therapeutic additives, humectants, and binding agents can be used as well.

The foam system of the present invention is stable in storage, e.g., it can be stored one or more years without noticeable effect on its desired properties. It is preferably stored in a closed container and at room temperature.

In use, the system of the present invention provides a unique and desirable combination of such properties as ease of use, aesthetic appearance, formulation stability, uniform distribution of active ingredients, ease of spreading and penetration, and release and availability of medication on contact with dermatomucosal surfaces.

The system is well-suited for the delivery of formulations that have not previously been delivered in the form of foams, for instance, for the delivery of hydrogen peroxide to the oral cavity. When used for cleansing minor wounds or irritations of the mouth or gums, a small amount of the foam is dispensed and applied to the affected area. It is allowed to remain in place for about 1 minute, and then expectorated. The foam can be used up to 4 times daily (after meals and at bedtime) or as directed by a dentist of physician. Children younger than 12 years of age should be supervised by an adult in the use of the foam, and for children younger than 2 years of age, a dentist or physician should be consulted prior to use.

The system is particularly well suited for the delivery of formulations that are not generally delivered in the form of foams, including for the delivery of dentifrices, including dental liquids, mouthwashes, oral lavages and gargles that contain hydrogen peroxide.

EXAMPLES

Example 1

Preparation of Systems and Formulations

Systems according to the present invention were prepared having sodium lauryl sulfate as a foaming agent and hydrogen peroxide as a cleansing or antiseptic agent. The ingredients were mixed in a variety of relative concentrations and a dispenser such as those described in the above-captioned '750 patent was filled with the formulations. The system was used by squeezing the container in order to generate a foam from the nozzle. At optimal concentrations as described herein the foam rapidly appeared in direct response to the pressure applied to the container. The foam was a stable one, in that it with little visible shrinkage, yet it when rubbed between the fingers or palms.

The foam system is useful for a wide variety of applications, and particularly for applications in which the use of hydrogen peroxide is indicated and where the use of liquid hydrogen peroxide is inconvenient or ineffective.

Example 2

Incorporation of Essential Oils

To 50 ml of water were added 0.1 g of methyl parabens as a preservative and 0.5 g of freeze-dried aloe. The mixture was stirred gently and to it was then added 0.5 ml of sodium lauryl sulfate. The solution was brought to 100 ml by the addition of water. Most cloudiness disappeared, although close inspection revealed oil droplets floating in the continuous aqueous phase. The liquid material was placed in a foaming container of the type described in U.S. Pat. No. 5,048,750. Operation of the container produced a stable, readily broken foam capable of being applied to the skin.

The present invention has been described with reference to various embodiments thereof. It will be apparent to those skilled in the art that many changes can be made in the embodiments described without departing from the scope of the present invention. Thus the scope of the present invention should not be limited to the formulations described in this application, but only by formulations described by the language of the claims and the equivalents of those formulations.

What is claimed is:

1. A system for delivering a chemical agent comprising a medicament in the form of an aerated foam, the system comprising a propellantless dispenser containing a foamable dental formulation comprising the chemical agent in the form of a solution or stable suspension and an aqueous solution of an anionic surface active agent as a foaming agent, said foaming agent being selected from the group consisting of cocomonoglyceride sulfonate, sodium lauryl sarcosinate, sodium dodecylbenzene sulfonate, dioctyl sodium sulfosuccinate, sodium lauryl sulfoacetate, sulfolaurate, 2-hydroxylalkyl sulfate, sodium lauryl sulfate, and the mixtures thereof.

2. A system for delivering a chemical agent comprising a medicament in the form of an aerated foam, the system comprising a propellantless dispenser containing a foamable dental formulation comprising the chemical agent in the form of a solution or stable suspension and an aqueous solution of an anionic surface active agent as a foaming agent.

3. A system for delivering a chemical agent comprising a medicament in the form of an aerated foam, the system comprising a propellantless dispenser containing a foamable dental formulation comprising the chemical agent in the form of a solution or stable suspension and an aqueous solution of an anionic surface active agent as a foaming agent, and said foamable formulation being a disinfecting solution.

4. A system according to claim 1 wherein the foamable formulation comprises hydrogen peroxide.

5. A system according to claim 2 wherein the dental formulation is selected from a group consisting of gargles, mouthwashes, and tooth cleaning formulations.

6. A system according to claim 1 wherein the dispenser and foamable formulation are capable of rapidly forming a stable but easily collapsible foam.

7. A system according to claim 1 wherein the foamable formulation further comprises aloe, present in a concentration of between about 0.1 and 1 g per 100 ml of formulation.

8. A system according to claim 1, wherein the foamable dental formulation further comprises essential oils and the anionic surface active agent comprises sodium lauryl sulfate, the sodium lauryl sulfate serving to hold the oils in solution or stable suspension.

9. A system according to claim 4 wherein the foamable formulation further comprises aloe, present in a concentration of between about 0.1 and 1 g per 100 ml of formulation.

10. A system according to claim 4, wherein the foamable formulation further comprises essential oils and the anionic surface active agent comprises sodium lauryl sulfate, the sodium lauryl sulfate serving to hold the oils in solution or stable suspension.

11. A system according to claim 4 wherein the dispenser comprises a device for producing and dispensing a foam and a container for the formulation, the device and container being operably connected in such a manner that the dispenser is capable of delivering the foam upon compression of the bottle.

12. A kit for delivering a chemical agent comprising
a medicament in the form of an aerated foam, the kit comprising a propellantless dispenser and a separately packaged volume of a foamable dental formulation comprising the chemical agent in the form of a solution or stable suspension and an aqueous solution of an anionic surface active agent as a foaming agent,
said foaming agent being selected from the group consisting of cocomonoglyceride sulfonate, sodium lauryl sarcosinate, sodium dodecylbenzene sulfonate, dioctyl sodium sulfosuccinate, sodium lauryl sulfoacetate, sulfolaurate, 2-hydroxyalkyl sulfate, sodium lauryl sulfate, and mixtures thereof.

13. A method for delivering a chemical agent comprising a medicament in the form of an aerated foam, comprising the steps of
providing a delivery system comprising a propellantless dispenser containing a foamable dental formulation comprising the chemical agent in the form of a solution or stable suspension and an aqueous solution of an anionic surface active agent as a foaming agent,
said foaming agent being selected from the group consisting of cocomonoglyceride sulfonate, sodium lauryl sarcosinate, sodium dodecylbenzene sulfonate, dioctyl sodium sulfosuccinate, sodium lauryl sulfoacetate, sulfolaurate, 2-hydroxyalkyl sulfate, sodium lauryl sulfate, and mixtures thereof.

14. A system for delivering a chemical agent comprising a medicament in the form of an aerated foam, the system comprising a propellantless dispenser for dispensing aerated foams, said dispenser containing a foamable aqueous dental formulation comprising the medicament and an anionic surface active agent as a foaming agent.

15. The system of claim 14 wherein the dental formulation is a gargle, mouthwash or tooth cleaning formulation.

16. The system of claim 14 wherein the surface active agent is sodium lauryl sulfate.

17. The system of claim 15 wherein the surface active agent is sodium lauryl sulfate.

18. A system for delivering a chemical agent comprising a medicament in the form of a foam, the system comprising a propellantless dispenser containing a foamable formulation comprising the chemical agent in the form of a solution or stable suspension and an aqueous solution of an anionic surface active agent as a foaming agent;
wherein said chemical agent is hydrogen peroxide;
wherein said surface active agent is sodium lauryl sulfate;
wherein said formulation is a dental formulation; and optionally containing essential oils and aloe.

* * * * *